(12) United States Patent
Chegini et al.

(10) Patent No.: US 10,786,264 B2
(45) Date of Patent: Sep. 29, 2020

(54) PERCUTANEOUS DISC CLEARING DEVICE

(71) Applicant: Medos International Sarl, Le Locle (CH)

(72) Inventors: Salman Chegini, Bern (CH); Joern Richter, Kandern (DE); Daniel Thommen, Liestal (CH)

(73) Assignee: Medos International Sarl, Le Locle (CH)

( * ) Notice: Subject to any disclaimer, the term of this patent is extended or adjusted under 35 U.S.C. 154(b) by 603 days.

(21) Appl. No.: 14/674,310

(22) Filed: Mar. 31, 2015

(65) Prior Publication Data

US 2016/0287264 A1 Oct. 6, 2016

(51) Int. Cl.
*A61B 17/16* (2006.01)
*A61B 17/32* (2006.01)
*A61B 17/00* (2006.01)

(52) U.S. Cl.
CPC ...... *A61B 17/1617* (2013.01); *A61B 17/1631* (2013.01); *A61B 17/1633* (2013.01); *A61B 17/1642* (2013.01); *A61B 17/1644* (2013.01); *A61B 17/1671* (2013.01); *A61B 17/32002* (2013.01); *A61B 2017/00261* (2013.01); *A61B 2017/00323* (2013.01); *A61B 2017/320032* (2013.01); *A61B 2217/005* (2013.01); *A61B 2217/007* (2013.01)

(58) Field of Classification Search
CPC ............ A61B 17/1631; A61B 17/1633; A61B 17/1644; A61B 17/1615; A61B 2017/00261; A61B 2017/320733
See application file for complete search history.

(56) References Cited

U.S. PATENT DOCUMENTS

| | | |
|---|---|---|
| 4,573,448 A | 3/1986 | Kambin |
| 4,646,738 A | 3/1987 | Trott |
| 4,678,459 A | 7/1987 | Onik et al. |
| 4,863,430 A | 9/1989 | Klyce et al. |
| 4,888,146 A | 12/1989 | Dandeneau |
| 5,080,662 A | 1/1992 | Paul |

(Continued)

FOREIGN PATENT DOCUMENTS

| | | |
|---|---|---|
| CN | 102727309 B | 11/2014 |
| DE | 94 15 039 U1 | 11/1994 |

(Continued)

OTHER PUBLICATIONS

International Search Report and Written Opinion for Application No. PCT/US2015/043554, dated Nov. 19, 2015 (8 pages).

(Continued)

*Primary Examiner* — Samuel S Hanna
(74) *Attorney, Agent, or Firm* — Nutter McClennen & Fish LLP

(57) ABSTRACT

A discectomy tool comprising:
a) a cannula having an outer surface having a longitudinal bore therein, a proximal end and a distal end;
b) a steering wire disposed in the longitudinal bore;
c) a flexible, hollow transmission shaft disposed in the cannula, the shaft having a throughbore, a proximal end portion, a distal end portion and an outer surface having a thread extending therefrom;
d) an irrigation source fluidly connected to the throughbore;
e) a cutting tip attached to the distal end portion of the transmission shaft.

5 Claims, 7 Drawing Sheets

(56) References Cited

U.S. PATENT DOCUMENTS

| | | |
|---|---|---|
| 5,195,541 A | 3/1993 | Obenchain |
| 5,285,795 A | 2/1994 | Ryan et al. |
| 5,395,317 A | 3/1995 | Kambin |
| 5,439,464 A | 8/1995 | Shapiro |
| 5,529,580 A | 6/1996 | Kusunoki et al. |
| 5,540,706 A | 7/1996 | Aust et al. |
| 5,569,290 A | 10/1996 | McAfee |
| 5,591,187 A | 1/1997 | Dekel |
| 5,601,569 A | 2/1997 | Pisharodi |
| 5,662,300 A | 9/1997 | Michelson |
| 5,688,222 A | 11/1997 | Hluchy et al. |
| 5,730,754 A | 3/1998 | Obenchain |
| 5,733,242 A | 3/1998 | Rayburn et al. |
| 5,735,792 A | 4/1998 | Vanden Hoek et al. |
| 5,820,623 A | 10/1998 | Ng |
| 5,885,300 A | 3/1999 | Tokuhashi et al. |
| 5,894,369 A | 4/1999 | Akiba et al. |
| 5,899,425 A | 5/1999 | Corey, Jr. et al. |
| 5,954,635 A | 9/1999 | Foley et al. |
| 6,053,907 A | 4/2000 | Zirps |
| 6,063,021 A | 5/2000 | Hossain et al. |
| 6,110,182 A | 8/2000 | Mowlai-Ashtiani |
| 6,200,322 B1 | 3/2001 | Branch et al. |
| 6,234,961 B1 | 5/2001 | Gray |
| 6,283,966 B1 | 9/2001 | Houfburg |
| 6,286,179 B1 | 9/2001 | Byrne |
| 6,296,644 B1 | 10/2001 | Saurat et al. |
| 6,322,498 B1 | 11/2001 | Gravenstein et al. |
| 6,354,992 B1 | 3/2002 | Kato |
| 6,371,968 B1 | 4/2002 | Kogasaka et al. |
| 6,383,191 B1 | 5/2002 | Zdeblick et al. |
| 6,447,446 B1 | 9/2002 | Smith et al. |
| 6,468,289 B1 | 10/2002 | Bonutti |
| 6,558,407 B1 | 5/2003 | Ivanko et al. |
| 6,575,899 B1 | 6/2003 | Foley et al. |
| 6,579,281 B2 | 6/2003 | Palmer et al. |
| 6,626,830 B1 | 9/2003 | Califiore et al. |
| 6,648,915 B2 | 11/2003 | Sazy |
| 6,676,597 B2 | 1/2004 | Guenst et al. |
| 6,688,564 B2 | 2/2004 | Salvermoser et al. |
| 6,758,809 B2 | 7/2004 | Briscoe et al. |
| 6,808,505 B2 | 10/2004 | Kadan |
| 6,887,198 B2 | 5/2005 | Phillips et al. |
| 6,983,930 B1 | 1/2006 | La Mendola et al. |
| 7,087,058 B2 | 8/2006 | Cragg |
| 7,104,986 B2 | 9/2006 | Hovda et al. |
| 7,137,949 B2 | 11/2006 | Scirica et al. |
| 7,182,731 B2 | 2/2007 | Nguyen et al. |
| 7,341,556 B2 | 3/2008 | Shalman |
| 7,434,325 B2 | 10/2008 | Foley et al. |
| 7,591,790 B2 | 9/2009 | Pflueger |
| 7,594,888 B2 | 9/2009 | Raymond et al. |
| 7,618,431 B2 | 11/2009 | Roehm, III et al. |
| 7,636,596 B2 | 12/2009 | Solar |
| 7,637,905 B2 | 12/2009 | Saadat et al. |
| 7,641,659 B2 | 1/2010 | Emstad et al. |
| 7,771,384 B2 | 8/2010 | Ravo |
| 7,794,456 B2 | 9/2010 | Sharps et al. |
| 7,811,303 B2 | 10/2010 | Fallin et al. |
| 7,931,579 B2 | 4/2011 | Bertolero et al. |
| 7,946,981 B1 | 5/2011 | Cubb |
| 7,951,141 B2 | 5/2011 | Sharps et al. |
| 7,959,564 B2 | 6/2011 | Ritland |
| 7,988,623 B2 | 8/2011 | Pagliuca et al. |
| 8,007,492 B2 | 8/2011 | DiPoto et al. |
| 8,038,606 B2 | 10/2011 | Otawara |
| 8,043,381 B2 | 10/2011 | Hestad et al. |
| 8,062,218 B2 | 11/2011 | Sebastian et al. |
| 8,092,464 B2 | 1/2012 | McKay |
| 8,096,944 B2 | 1/2012 | Harrel |
| 8,202,216 B2 | 6/2012 | Melkent et al. |
| 8,236,006 B2 | 8/2012 | Hamada |
| 8,333,690 B2 | 12/2012 | Ikeda |
| 8,360,970 B2 | 1/2013 | Mangiardi |
| 8,372,131 B2 | 2/2013 | Hestad et al. |
| 8,382,048 B2 | 2/2013 | Nesper et al. |
| 8,397,335 B2 | 3/2013 | Gordin et al. |
| 8,435,174 B2 | 5/2013 | Cropper et al. |
| 8,460,180 B1 | 6/2013 | Zarate et al. |
| 8,460,186 B2 | 6/2013 | Ortiz et al. |
| 8,460,310 B2 | 6/2013 | Stern |
| 8,518,087 B2 | 8/2013 | Lopez et al. |
| 8,535,220 B2 | 9/2013 | Mondschein |
| 8,556,809 B2 | 10/2013 | Vijayanagar |
| 8,585,726 B2 | 11/2013 | Yoon et al. |
| 8,602,979 B2 | 12/2013 | Kitano |
| 8,622,894 B2 | 1/2014 | Banik et al. |
| 8,636,655 B1 | 1/2014 | Childs |
| 8,690,764 B2 | 4/2014 | Clark et al. |
| 8,721,536 B2 | 5/2014 | Marino et al. |
| 8,740,779 B2 | 6/2014 | Yoshida |
| 8,784,421 B2 | 7/2014 | Carrison et al. |
| 8,821,378 B2 | 9/2014 | Morgenstern Lopez et al. |
| 8,834,507 B2 | 9/2014 | Mire et al. |
| 8,845,734 B2 | 9/2014 | Weiman |
| 8,852,242 B2 | 10/2014 | Morgenstern Lopez et al. |
| 8,870,753 B2 | 10/2014 | Boulais et al. |
| 8,870,756 B2 | 10/2014 | Maurice |
| 8,876,712 B2 | 11/2014 | Yee et al. |
| 8,894,573 B2 | 11/2014 | Loftus et al. |
| 8,894,653 B2 | 11/2014 | Solsberg et al. |
| 8,926,502 B2 | 1/2015 | Levy et al. |
| 8,932,207 B2 | 1/2015 | Greenburg et al. |
| 8,932,360 B2 | 1/2015 | Womble et al. |
| 8,936,605 B2 | 1/2015 | Greenberg |
| 8,974,381 B1 | 3/2015 | Lovell et al. |
| 8,986,199 B2 | 3/2015 | Weisenburgh, II et al. |
| 8,992,580 B2 | 3/2015 | Bar et al. |
| 9,028,522 B1 | 5/2015 | Prado |
| 9,050,146 B2 | 6/2015 | Woolley et al. |
| 9,055,936 B2 | 6/2015 | Mire et al. |
| 9,072,431 B2 | 7/2015 | Adams et al. |
| 9,078,562 B2 | 7/2015 | Poll et al. |
| 9,131,948 B2 | 9/2015 | Fang et al. |
| 9,144,374 B2 | 9/2015 | Maurice, Jr. |
| 9,198,674 B2 | 12/2015 | Benson et al. |
| 9,211,059 B2 | 12/2015 | Drach et al. |
| 9,216,016 B2 | 12/2015 | Fiechter et al. |
| 9,216,125 B2 | 12/2015 | Sklar |
| 9,232,935 B2 | 1/2016 | Brand et al. |
| 9,247,997 B2 | 2/2016 | Stefanchik et al. |
| 9,265,491 B2 | 2/2016 | Lins et al. |
| 9,277,928 B2 | 3/2016 | Morgenstern Lopez |
| 9,307,972 B2 | 4/2016 | Lovell et al. |
| 9,320,419 B2 | 4/2016 | Kirma et al. |
| RE46,007 E | 5/2016 | Banik et al. |
| RE46,062 E | 7/2016 | James et al. |
| 9,386,971 B1 | 7/2016 | Casey et al. |
| 9,387,313 B2 | 7/2016 | Culbert et al. |
| 9,414,828 B2 | 8/2016 | Abidin et al. |
| 9,486,296 B2 | 11/2016 | Mire et al. |
| 9,492,194 B2 | 11/2016 | Morgenstern Lopez et al. |
| 9,510,853 B2 | 12/2016 | Aljuri et al. |
| 9,526,401 B2 | 12/2016 | Saadat et al. |
| 9,579,012 B2 | 2/2017 | Vazales et al. |
| 9,603,510 B2 | 3/2017 | Ammirati |
| 9,603,610 B2 | 3/2017 | Richter et al. |
| 9,610,007 B2 | 4/2017 | Kienzle et al. |
| 9,610,095 B2 | 4/2017 | To |
| 9,629,521 B2 | 4/2017 | Ratnakar |
| 9,655,605 B2 | 5/2017 | Serowski et al. |
| 9,655,639 B2 | 5/2017 | Mark |
| 9,668,643 B2 | 6/2017 | Kennedy, II et al. |
| 9,675,235 B2 | 6/2017 | Lieponis |
| 9,700,378 B2 | 7/2017 | Mowlai-Ashtiani |
| 9,706,905 B2 | 7/2017 | Levy |
| 2002/0022762 A1 | 2/2002 | Beane et al. |
| 2002/0138020 A1 | 9/2002 | Pflueger |
| 2003/0083555 A1 | 5/2003 | Hunt et al. |
| 2003/0171744 A1 | 9/2003 | Leung et al. |
| 2003/0191474 A1 | 10/2003 | Cragg et al. |
| 2004/0122446 A1 | 6/2004 | Solar |
| 2004/0127992 A1 | 7/2004 | Serhan et al. |
| 2004/0143165 A1 | 7/2004 | Alleyne |

(56) References Cited

U.S. PATENT DOCUMENTS

| | | |
|---|---|---|
| 2005/0085692 A1 | 4/2005 | Kiehn et al. |
| 2005/0090848 A1 | 4/2005 | Adams |
| 2005/0187570 A1 | 8/2005 | Nguyen et al. |
| 2005/0256525 A1 | 11/2005 | Culbert et al. |
| 2006/0206118 A1 | 9/2006 | Kim et al. |
| 2007/0055259 A1 | 3/2007 | Norton et al. |
| 2007/0129634 A1 | 6/2007 | Hickey et al. |
| 2007/0149975 A1 | 6/2007 | Oliver et al. |
| 2007/0203396 A1 | 8/2007 | McCutcheon et al. |
| 2007/0225556 A1 | 9/2007 | Ortiz et al. |
| 2007/0260113 A1 | 11/2007 | Otawara |
| 2008/0004646 A1 | 1/2008 | To et al. |
| 2008/0015621 A1 | 1/2008 | Emanuel |
| 2008/0033251 A1 | 2/2008 | Araghi |
| 2008/0081951 A1 | 4/2008 | Frasier et al. |
| 2008/0188714 A1 | 8/2008 | McCaffrey |
| 2009/0018566 A1 | 1/2009 | Escudero et al. |
| 2009/0024158 A1 | 1/2009 | Viker |
| 2009/0062871 A1 | 3/2009 | Chin et al. |
| 2009/0105543 A1 | 4/2009 | Miller et al. |
| 2009/0156898 A1 | 6/2009 | Ichimura |
| 2009/0187080 A1 | 7/2009 | Seex |
| 2009/0240111 A1 | 9/2009 | Kessler et al. |
| 2009/0287061 A1 | 11/2009 | Feigenbaum et al. |
| 2009/0318765 A1 | 12/2009 | Torii |
| 2010/0004651 A1 | 1/2010 | Biyani |
| 2010/0022841 A1 | 1/2010 | Takahashi et al. |
| 2010/0076476 A1 | 3/2010 | To et al. |
| 2010/0114147 A1 | 5/2010 | Biyani |
| 2010/0151161 A1 | 6/2010 | Da Rolo |
| 2010/0161060 A1 | 6/2010 | Schaller et al. |
| 2010/0256446 A1 | 10/2010 | Raju |
| 2010/0280325 A1 | 11/2010 | Ibrahim et al. |
| 2010/0284580 A1 | 11/2010 | OuYang et al. |
| 2010/0286477 A1 | 11/2010 | OuYang et al. |
| 2010/0312053 A1 | 12/2010 | Larsen |
| 2011/0028791 A1 | 2/2011 | Marino et al. |
| 2011/0054507 A1 | 3/2011 | Batten et al. |
| 2011/0087257 A1* | 4/2011 | To .................... A61B 17/1617 606/170 |
| 2011/0106261 A1 | 5/2011 | Chin et al. |
| 2011/0125158 A1 | 5/2011 | Diwan et al. |
| 2011/0130634 A1 | 6/2011 | Solitario, Jr. et al. |
| 2011/0295070 A1 | 12/2011 | Yasunaga |
| 2011/0319941 A1 | 12/2011 | Bar et al. |
| 2012/0095296 A1 | 4/2012 | Trieu et al. |
| 2012/0101338 A1 | 4/2012 | O'Prey et al. |
| 2012/0172905 A1* | 7/2012 | Lee Shee ......... A61B 17/32002 606/180 |
| 2012/0209273 A1 | 8/2012 | Zaretzka et al. |
| 2012/0221007 A1 | 8/2012 | Batten et al. |
| 2012/0232350 A1 | 9/2012 | Seex |
| 2012/0232552 A1 | 9/2012 | Morgenstern Lopez et al. |
| 2012/0259213 A1 | 10/2012 | Conquergood et al. |
| 2012/0298820 A1 | 11/2012 | Manolidis |
| 2012/0316400 A1 | 12/2012 | Vijayanagar |
| 2013/0103067 A1 | 4/2013 | Fabro et al. |
| 2013/0103103 A1 | 4/2013 | Mire et al. |
| 2013/0150670 A1 | 6/2013 | O'Prey et al. |
| 2013/0150674 A1 | 6/2013 | Haig et al. |
| 2013/0172676 A1 | 7/2013 | Levy et al. |
| 2013/0282022 A1 | 10/2013 | Yousef |
| 2013/0289399 A1 | 10/2013 | Choi et al. |
| 2013/0303846 A1 | 11/2013 | Cybulski et al. |
| 2014/0066940 A1 | 3/2014 | Fang et al. |
| 2014/0074170 A1 | 3/2014 | Mertens et al. |
| 2014/0142584 A1 | 5/2014 | Sweeney |
| 2014/0148647 A1 | 5/2014 | Okazaki |
| 2014/0180321 A1 | 6/2014 | Dias et al. |
| 2014/0194697 A1 | 7/2014 | Seex |
| 2014/0215736 A1 | 8/2014 | Gomez et al. |
| 2014/0257489 A1 | 9/2014 | Warren et al. |
| 2014/0275799 A1 | 9/2014 | Schuele |
| 2014/0276840 A1* | 9/2014 | Richter ............. A61B 17/1671 606/80 |
| 2014/0277204 A1 | 9/2014 | Sandhu |
| 2014/0318582 A1 | 10/2014 | Mowlai-Ashtiani |
| 2014/0357945 A1 | 12/2014 | Duckworth |
| 2015/0018623 A1 | 1/2015 | Friedrich et al. |
| 2015/0065795 A1 | 3/2015 | Titus |
| 2015/0073218 A1 | 3/2015 | Ito |
| 2015/0112398 A1 | 4/2015 | Morgenstern Lopez et al. |
| 2015/0164496 A1 | 6/2015 | Karpowicz et al. |
| 2015/0216593 A1 | 8/2015 | Biyani |
| 2015/0223676 A1 | 8/2015 | Bayer et al. |
| 2015/0230697 A1 | 8/2015 | Phee et al. |
| 2015/0342621 A1 | 12/2015 | Jackson, III |
| 2015/0374213 A1 | 12/2015 | Maurice, Jr. |
| 2016/0015467 A1 | 1/2016 | Vayser et al. |
| 2016/0030061 A1 | 2/2016 | Thommen et al. |
| 2016/0066965 A1 | 3/2016 | Chegini et al. |
| 2016/0067003 A1 | 3/2016 | Chegini et al. |
| 2016/0074029 A1 | 3/2016 | O'Connell et al. |
| 2016/0095505 A1 | 4/2016 | Johnson et al. |
| 2016/0106408 A1 | 4/2016 | Ponmudi et al. |
| 2016/0166135 A1 | 6/2016 | Fiset |
| 2016/0174814 A1 | 6/2016 | Igov |
| 2016/0213500 A1 | 7/2016 | Beger et al. |
| 2016/0228280 A1 | 8/2016 | Schuele et al. |
| 2016/0235284 A1 | 8/2016 | Yoshida et al. |
| 2016/0296220 A1 | 10/2016 | Mast et al. |
| 2016/0353978 A1 | 12/2016 | Miller et al. |
| 2017/0003493 A1 | 1/2017 | Zhao |
| 2017/0007226 A1 | 1/2017 | Fehling |
| 2017/0027606 A1 | 2/2017 | Cappelleri et al. |
| 2017/0042408 A1 | 2/2017 | Washburn et al. |
| 2017/0042411 A1 | 2/2017 | Kang et al. |
| 2017/0065269 A1 | 3/2017 | Thommen et al. |
| 2017/0065287 A1 | 3/2017 | Silva et al. |
| 2017/0071610 A1* | 3/2017 | Lynch ................ A61B 17/1635 |
| 2017/0086939 A1 | 3/2017 | Vayser et al. |
| 2017/0135699 A1 | 5/2017 | Wolf |
| 2017/0156755 A1 | 6/2017 | Poll et al. |
| 2017/0156814 A1 | 6/2017 | Thommen et al. |
| 2017/0196549 A1 | 7/2017 | Piskun et al. |
| 2017/0224391 A1 | 8/2017 | Biester et al. |

FOREIGN PATENT DOCUMENTS

| | | |
|---|---|---|
| DE | 299 16 026 U1 | 11/1999 |
| EP | 0 537 116 A1 | 4/1993 |
| EP | 0 807 415 A2 | 11/1997 |
| GB | 2481727 A | 1/2012 |
| JP | 2001-517474 A | 10/2001 |
| JP | 2011-528962 A | 12/2011 |
| JP | 2014-507188 A | 3/2014 |
| WO | 93/04634 A1 | 3/1993 |
| WO | 96/29014 A1 | 9/1996 |
| WO | 1999015090 A1 | 4/1999 |
| WO | 01/56490 A1 | 8/2001 |
| WO | 01/89371 A1 | 11/2001 |
| WO | 02/02016 A1 | 1/2002 |
| WO | 2004/103430 A2 | 12/2004 |
| WO | 2008/121162 A1 | 10/2008 |
| WO | 2009/033207 A1 | 3/2009 |
| WO | 201011956 A1 | 1/2010 |
| WO | 2013/033426 A2 | 3/2013 |
| WO | 2013/059640 A1 | 4/2013 |
| WO | 2014/050236 A1 | 4/2014 |
| WO | 2014/100761 A2 | 6/2014 |
| WO | 2014/185334 A1 | 11/2014 |
| WO | 2015/138432 A1 | 9/2015 |
| WO | 2016/111373 A1 | 7/2016 |
| WO | 2016/131077 A1 | 8/2016 |
| WO | 2016/168673 A1 | 10/2016 |
| WO | 2017/006684 A1 | 1/2017 |
| WO | 2017/015480 A1 | 1/2017 |
| WO | 2017/083648 A1 | 5/2017 |

OTHER PUBLICATIONS

International Search Report and Written Opinion for Application No. PCT/US2015/048485, dated Feb. 9, 2016. (16 pages).

(56) References Cited

OTHER PUBLICATIONS

International Search Report and Written Opinion for Application No. PCT/US2015/060978, dated Feb. 15, 2016 (8 pages).
Invitation to Pay Additional Fees for Application No. PCT/US2016/050022, dated Nov. 3, 2016 (2 pages).
International Search Report and Written Opinion for Application No. PCT/US2016/050022, dated Feb. 1, 2017 (19 pages).
Iprenburg, M, "Percutaneous Transforaminal Endoscopic Discectomy: The Thessys Method," in Lewandrowski, K., et al, Minimally Invasive Spinal Fusion Techniques, Summit Communications, 2008 pp. 65-81.
Jung, K., et al., "A hands-free region-of-interest selection interface for solo surgery with a wide-angle endoscope: preclinical proof of concept," Surg Endosc, 2017, v. 31, pp. 974-980.
Extended European Search Report for Application No. 19152080.8, dated Apr. 4, 2019 (9 pages).
Japanese Office Action for Application No. 2017-551320, dated Jan. 7, 2020 (4 pages).

\* cited by examiner

FIG. 1
FIG. 2
FIG. 3
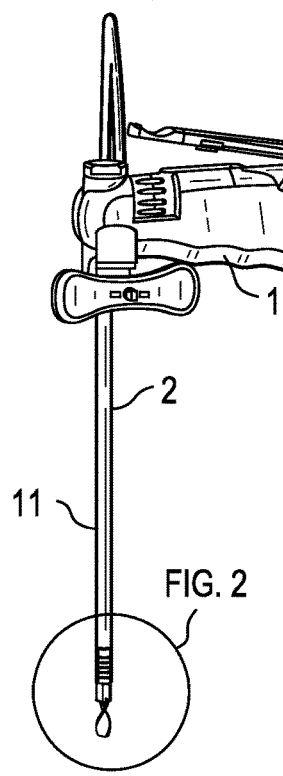
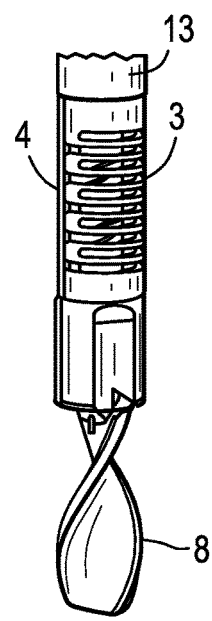
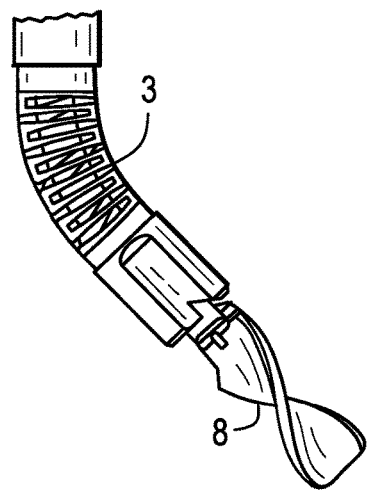
FIG. 4A
FIG. 4B
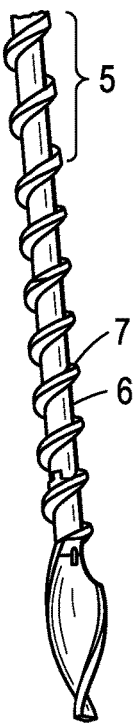
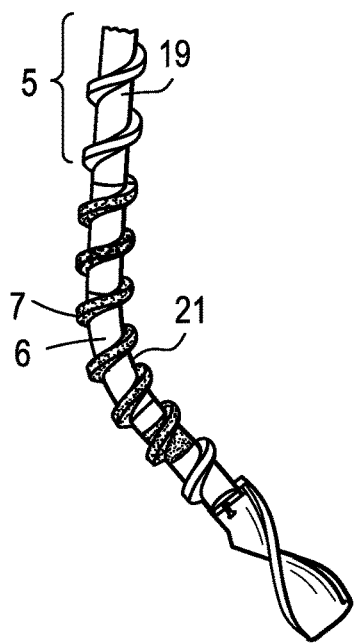

PERCUTANEOUS DISC CLEARING DEVICE

BACKGROUND OF THE INVENTION

Lumbar interbody fusion is a surgical procedure that is often performed up on instabilities within the lumbar spine. These instabilities are either the result of a medical condition like degenerative disc disease (DDD) or a vertebral bone fracture, or the result of a surgical decompression procedure treating stenosis, in which soft tissue and/or bony structures around compressed neural structures in the spine are removed. To achieve an acceptable interbody fusion, the existing disc needs to be removed (discectomy), and bone graft and/or an implanted cage is put on its place.

There are several approaches through which the disc clearing and cage insertion steps can be performed, each with its benefits and risks. One of the most popular is the transforaminal approach, commonly used in a transforaminal lumbar interbody fusion (TLIF).

In a TLIF approach, the creation of an access window that is necessary to insert the cage (implant) normally requires the removal of parts of the facet joint, and takes time. Moreover, the iatrogenic trauma produces by this procedure induces a significant amount of destabilization and recovery time.

If there were a possibility of performing the whole interbody fusion procedure through a percutaneous or endoscopic working channel, the iatrogenic trauma, risk of neural damage during the access and fusion procedure, surgery time and most probably the infection risk might be significantly reduced.

The current standard disc clearing step in a fusion surgery is a very manually-intensive procedure, and requires about sixty instrument passes close to the dura and nerve roots, in which instruments like rongeurs and curettes transport the excised material out of the patient. Today, it is difficult to perform such clearing through a percutaneous working channel of 4-12 mm outer diameter. Therefore, it is a goal to eliminate the need for continuous instrument passes close to the nerves.

Problems associated with convention discectomy devices include inefficient tissue cutting, clotting and inability to be steered.

The following references disclose discectomy tools: U.S. Pat. Nos. 5,285,795; 4,863,430; US2011-054507; US2010-076476; US2013-0103067; US2008-0015621; US2012-0221007; US2005-0090848; US2012-0209273; US2006-0206118; 5,540,706; 6,053,907; 5,591,187; 4,646,738; US2002-0138020; US2007-0055259; 5,529,580; US2007-0149975; US2003-0191474; US2010-0151161; 4,678,459; 5,195,541; US2004-0127992; US2003-0171744; US2010-0161060; 8,784,421; 6,468,289; WO 09-033207; WO 2014-100761; and 8,585,726.

SUMMARY OF THE INVENTION

There is provided a discectomy device that can be introduced through a small working channel (diameter 4-12 mm). The working channel is introduced through a variety of possible approaches (e.g. ELIF/TLIF/lateral) so that the distal end of the working channel extends a few millimeters into the annulus of the (lumbar) disc. When the device is fully introduced into the working channel, its drill-like tip is located fully within the disc (i.e., this tip exceeds the distal end of the working channel).

Preferably, the drill-like tip of the device can rotate and is powered. The tip's geometry enables cutting and detaching disc material (nucleus pulposus and inner annulus). More preferably, the cutting tip is that discloses in USSN S01984S, the specification of which is incorporated by reference in its entirety.

The device has sufficient flexibility to be steered actively and to sweep and detach disc material at locations. In contrast, a relatively stiff instrument—if introduced through the same limited-flexibility working channel—could never reach those locations. The device preferably has the necessary steering stability and bending radius to reach and clear a sufficient amount of disc area so as to permit the subsequent placement of bone graft material therein in order to reach a stable fusion.

In some embodiments of the present invention, the discectomy device has a combination of the following design elements:

a cutting blade geometry disclosed in US 2014-0276840), the specification of which is incorporated by reference in its entirety;

a thin-walled, steerable outer cannula steered by "push-pull" dovetail-steering-strips;

a flexible and torque-transmitting drive shaft, containing a flexible auger-based disc tissue-transport system;

central irrigation provided through the drive shaft and exiting at the cutting blade to prevent tissue-clotting at the blade or along the auger; and suction means to support auger for transporting the mix of irrigation solution and disc material.

The present invention helps to improve the discectomy aspects of the current standard lumbar interbody fusion procedure by enabling the disc clearing step to be performed percutaneously or through an endoscopic working channel, and by enabling the disc clearing step through a standard or mini-open approach (TLIF, ELIF/lateral approach) to be performed automated, safer and faster than with today's standard manual tools.

In some embodiments of the present invention, the percutaneous disc clearing tool can be inserted through a straight or curved, rigid percutaneous working channel (inner diameter range about 4-12 mm, ideally about 5-7.5 mm), having a steerable disc removal member exiting the working channel and being located fully or partly within the vertebral disc.

The disc removal tool can be manually driven or powered, and it has the ability to detach (rupture or cut) nucleus as well as annulus material within the intervertebral disc. Such disc removal mechanisms have been previously described.

The disc removal tool can be actively steered, so that it can sweep within the disc, and detach disc material at locations where a stiff instrument (if introduced through the same working channel) could never reach. The disc removal member has the necessary steering stability and bending radius to reach and clear a sufficient amount of disc area, while being introduced and operated through a rigid and straight working channel.

The cut material can be transported out of the disc, leaving a cavity in the disc that is big enough to allow interbody stabilization & fusion.

Therefore, in accordance with the present invention, there is provided a discectomy tool comprising:

a) a cannula having an outer surface having a longitudinal bore therein, a proximal end portion and a distal end portion;

b) a steering wire longitudinally contacting the cannula and extending in the direction of the longitudinal bore;

c) a flexible, hollow transmission shaft disposed in the cannula, the shaft having a throughbore, a proximal end portion, a distal end portion and an outer surface having a thread extending therefrom;
d) an irrigation source fluidly connected to the throughbore;
e) a cutting tip attached to the distal end portion of the transmission shaft;

Also in accordance with the present invention, there is provided a discectomy tool comprising:
a) a cannula having an outer surface having a longitudinal bore therein, a proximal end and a distal end;
b) a transmission shaft having a proximal end portion and a distal end portion;
c) a rotatable cutting tip attached to the distal end portion of the transmission shaft; and
d) a flexible helical auger having a proximal end portion, and intermediate portion and a distal end portion, wherein the intermediate portion is loosely wrapped around the flexible torque transmission shaft,
wherein the transmission shaft and auger are adapted to rotate within the longitudinal bore of the cannula, wherein the cutting tip extends out the bore at the distal end of the cannula.

Also in accordance with the present invention, there is provided a discectomy tool comprising:
a) a cannula having an outer surface having a longitudinal bore therein, a proximal end and a distal end;
b) a transmission shaft having a proximal end portion and a distal end portion;
c) a rotatable cutting tip attached to the distal end portion of the transmission shaft; and
d) a flexible helical auger having a proximal end portion, a hollow intermediate portion and a distal end portion, wherein the proximal end portion of the auger is connected to the torque transmission shaft and the distal end portion of the auger is connected to the cutting tip,
wherein the transmission shaft and auger are adapted to rotate within the longitudinal bore of the cannula, wherein the cutting tip extends out the bore at the distal end of the cannula.

Also in accordance with the present invention, there is provided a discectomy tool comprising:
a) a cannula having a proximal end, a distal end, and an outer surface having a first longitudinal recess therein;
b) a transmission shaft disposed in the cannula, the shaft having a proximal end portion and a distal end portion;
c) a cutting tip attached to the distal end portion of the transmission shaft;
d) a first steering element disposed in the first longitudinal recess of the outer surface.

Also in accordance with the present invention, there is provided a discectomy tool comprising:
a) a cannula having a proximal end, a distal end, and an outer surface;
b) a transmission shaft disposed in the cannula, the shaft having a proximal end portion and a distal end portion;
c) a cutting tip attached to the distal end portion of the transmission shaft;
d) first and second steering elements bilaterally and longitudinally disposed on the outer surface of the cannula.

Also in accordance with the present invention, there is provided a discectomy tool comprising:
a) a cannula having a proximal end portion, a distal end portion, and an outer surface; the cannula having a first longitudinal face and a second opposed longitudinal face, wherein the first longitudinal face has a plurality of alternating, opposed transverse cutouts therealong to form a first substantially square wave of the first longitudinal face, (and preferably, the second longitudinal face has a plurality of alternating, opposed transverse cutouts therealong to form a second substantially square wave of the second longitudinal face,)
b) a transmission shaft disposed in the cannula, the shaft having a proximal end portion and a distal end portion;
c) a cutting tip attached to the distal end portion of the transmission shaft.

DESCRIPTION OF THE FIGURES

FIG. 1 discloses an embodiment of a discectomy tool of the present invention.
FIGS. 2 and 3 disclose a distal portion of an embodiment of a discectomy tool of the present invention.
FIGS. 4A-4B disclose embodiments of a transmission shaft of the present invention.

DETAILED DESCRIPTION OF THE INVENTION

Figure 5A:
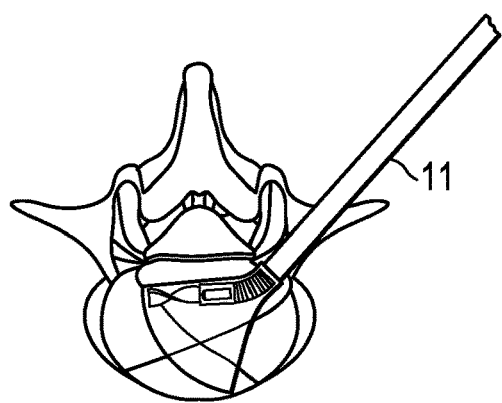
FIGS. 5A-F disclose approaches used by a discectomy tool of the present invention in a disc space.

Referring now to FIGS. 1-4B, there is provided a discectomy tool comprising:
a) a cannula 11 having an outer surface 13 having a longitudinal bore therein, a rigid proximal end portion 2 and a flexible distal end portion 3;
b) a steering wire 4 longitudinally contacting the cannula and extending in the direction of the longitudinal bore;
c) a flexible, hollow transmission shaft 5 disposed in the cannula, the shaft having a throughbore, a proximal end portion 19, a flexible 6 distal end portion and an outer surface 21 having a flexible thread 7 extending therefrom;
d) an irrigation source fluidly connected to the throughbore;

e) a cutting tip 8 attached to the distal end portion of the transmission shaft; and f) a drive/steer/irrigation handle 1.

Figure 5B:
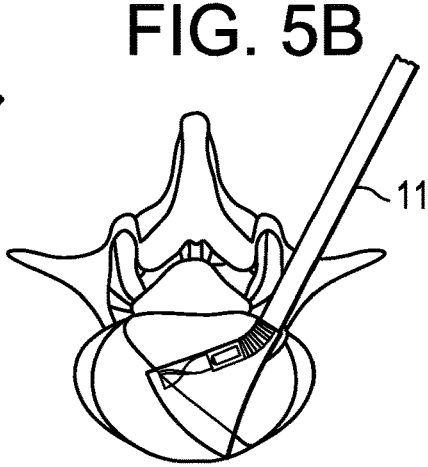
Figure 5C:
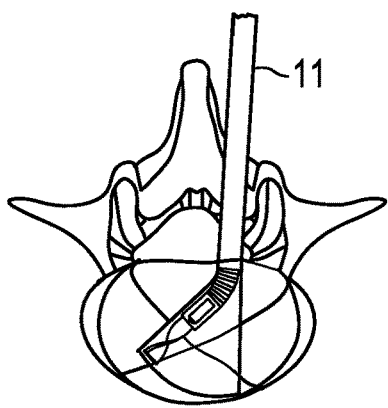
Figure 5D:
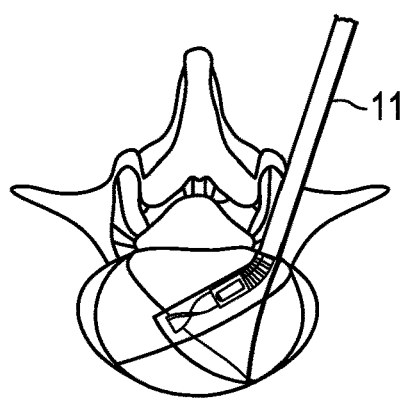
Figure 5E:
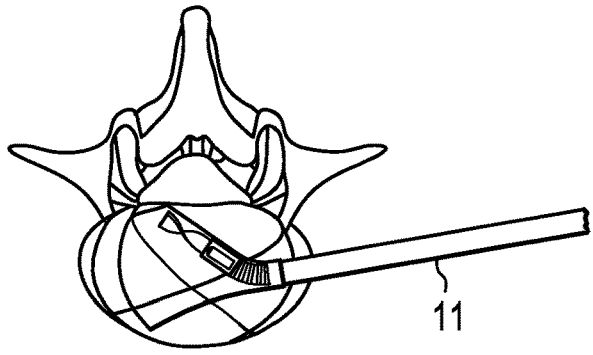
Figure 5F:
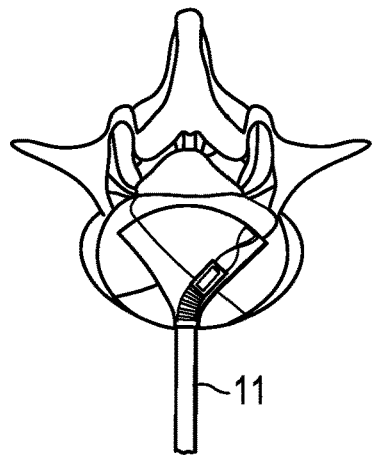

The invention is not limited to any particular approach trajectory of the working channel. For example, if a certain approach/trajectory offers an advantage in a given situation, the approach can be chosen accordingly. For example, and now referring to FIGS. 5A-5F, the surgeon may desire to use the tool in the following non-limiting approaches:

a) a flat angle extraforaminal approach (FIG. 5A);

b) a steep extraformainal approach (FIG. 5B);

c) a translaminar approach (FIG. 5C);

d) a transformainal approach (FIG. 5D);

e) a far lateral approach (FIG. 5E); and f) an anterior approach (FIG. 5F).

In order to increase the cleared volume of the disc, the tool can be serially inserted from multiple approaches, e.g. from two opposite sides of the disc. In a serial embodiment, one side of the disc is cleared and then the other side is cleared. In a simulataneous embodiment, the two sides of the disc are cleared simultaneously.

The working channel can be straight or bent. Also, the cross sectional area of the working channel can vary (e.g., it can be a funnel-shaped working channel).

In use, in some embodiments, the distal end portion of the tool can be swept side-to-side without longitudinal movement. In other embodiments, the distal end portion of the tool can be swept side-to-side with simultaneous unidirectional longitudinal movement. In other embodiments, the distal end portion of the tool can be swept side-to-side with simultaneous longitudinal back-and-forth movement.

In some embodiments, the tool of the present invention is used to clear a disc. In others, it is used to clean disc endplates abutting the disc. In still others, it is used to both clear a disc and clear its associated endplates.

Figure 6:
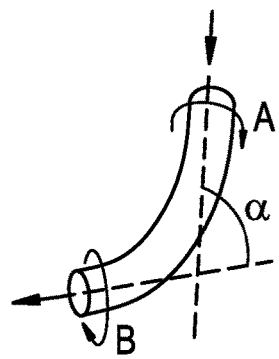
FIGS. 6-8 disclose embodiments of bent transmission shafts of the present invention.
Figure 7:
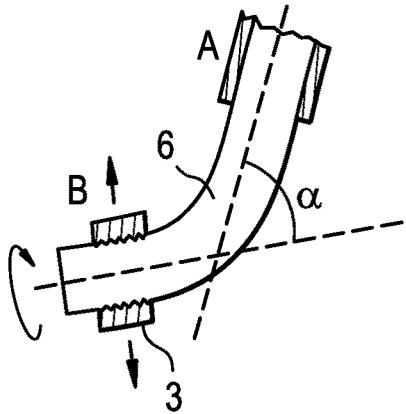
Figure 8:
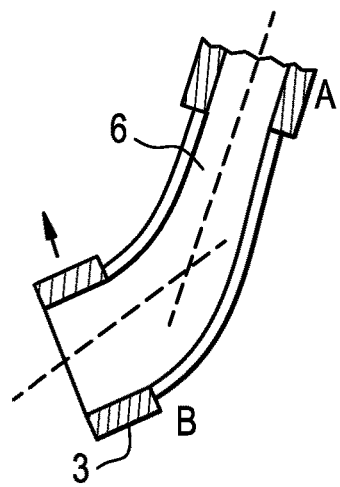
Figure 9:
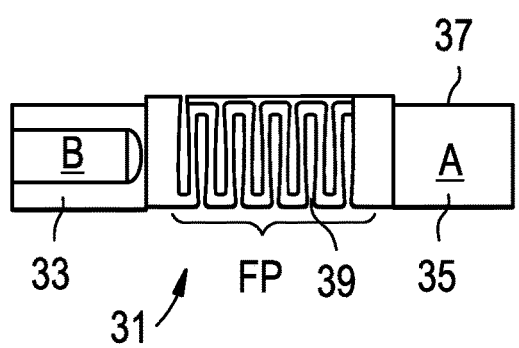
FIGS. 9-11B disclose embodiments of cannulae of the present invention.
Figure 10:
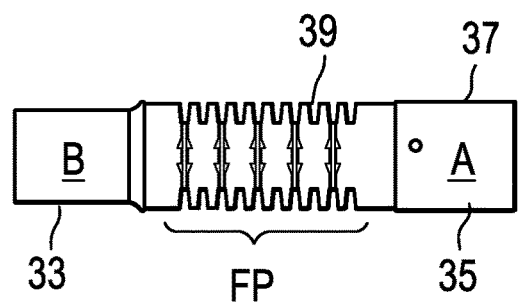

Now referring to FIGS. 6-8, one goal of the present invention is to guide and steer a rotating, curved flexible transmission shaft that has to transmit an incoming Torque $M_{in}$ (from the first right cylindrical portion A), in order to reach an outgoing torque $M_{out}$ at the second right cylindrical portion B, where A and B are not always concentric, but oriented against each other over a certain (variable) angle α and have a flexible, curved portion inbetween (see FIG. 6). In order to accomplish this goal, the steering cannula needs to be able to guide both straight transmission shaft portions A and B, but also to connect these guiding zones and actively change the angle between them (see FIG. 7) Merely providing the steering cannula with one or two joints between A and B would not be satisfactory because the joint geometry might interfere with the inner, rotating flexible shaft. Rather, because of the importance of optimizing the material transport and torque transmission, it is believed the inner rotating flexible shaft needs to have a smooth transition shape between portions A and B (i.e., no joints). Consistent with that desire is a belief that the steering cannula must also have a smooth transition shape in order to minimize interference and to maximize the guidance (as shown by the dotted line in FIG. 8). Merely providing a simple elastic tube as the flexible part (FP) of the cannula probably does not provide enough stability and at the same time enough flexibility.

Therefore, it is believed that the outer cannula should be stable against axial torsion, but bendable in one plane. It is further believed that the cannula geometry disclosed in FIGS. 9-11B, consisting of alternating bullet-shaped cutouts, provides these desired qualities. Adequate detailed dimensioning of the cutout geometry can adjust and optimize the stiffness/stability, steering angle, steering radius of the cannula.

Referring now to FIG. 9-11C, there is provided a discectomy tool comprising:

a) a cannula 31 having a proximal end portion 33, a distal end portion 35, and an outer surface 37; the cannula having a first longitudinal face 38 and a second opposed longitudinal face, wherein the first longitudinal face has a plurality of alternating, opposed transverse cutouts 39 therealong to form a substantially square wave 36 of the first longitudinal face, b) a transmission shaft disposed in the cannula, the shaft having a proximal end portion and a distal end portion;

c) a cutting tip attached to the distal end portion of the transmission shaft.

Figure 11A:
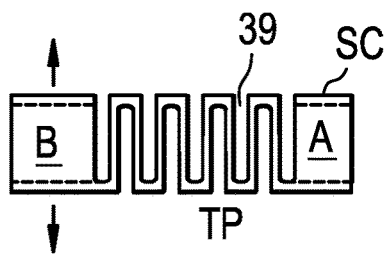
FIG. 11C discloses a cross-sectional view of a cannula embodiment of the present invention.
FIG. 11D discloses a side view of a cannula embodiment of the present invention, revealing a first longitudinal face of the cannula.
Figure 11B:
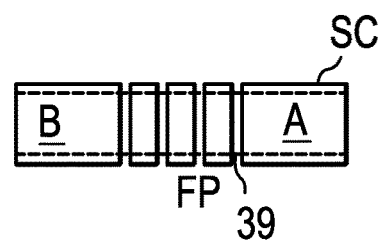
Figure 11D:
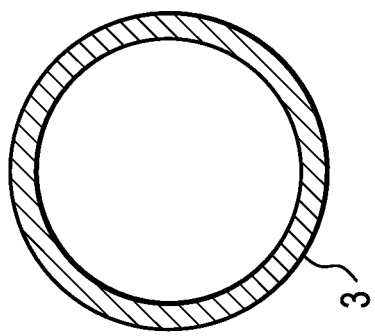
Figure 11C:
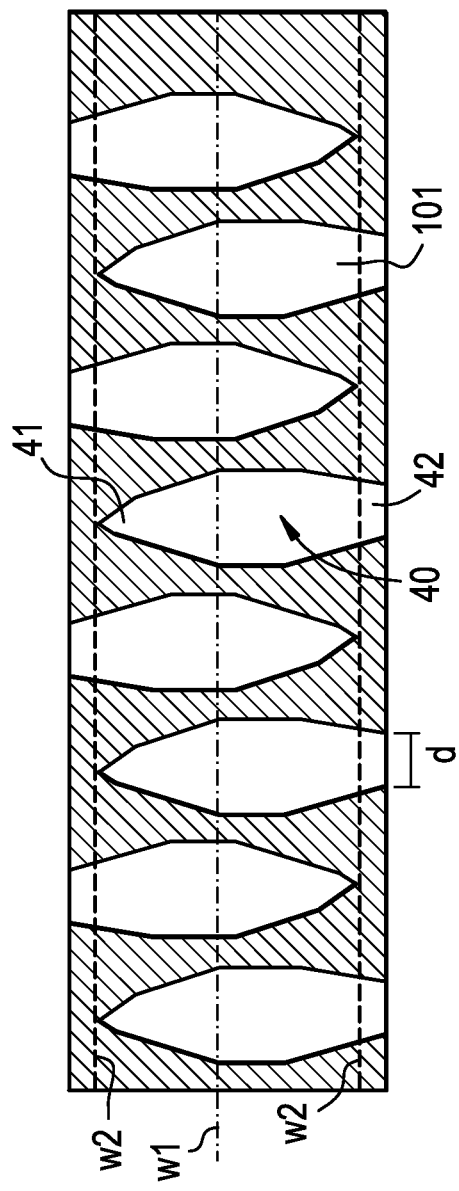

Now referring to FIG. 11D, preferably, the cutouts 101 have a tapered distal end portion 41 so as to form a bullet shape. Also preferably, the width of the middle portion 40 of the cutout is greater than the width of either the proximal end portion 42 or the distal end portion 41.

Figure 12:
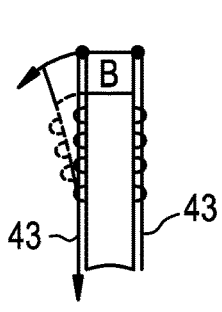
FIGS. 12-13 disclose cannulae with longitudinal steering elements.
Figure 13:
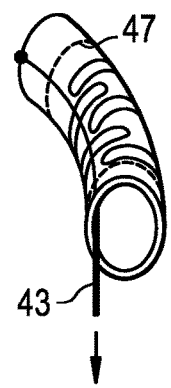
Figure 16:
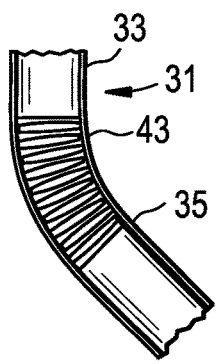
FIGS. 16-17 disclose cannulae with longitudinal steering elements.
Figure 17:
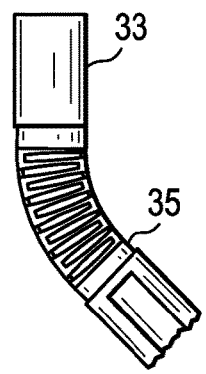
Figure 18:
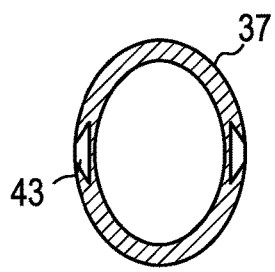
FIGS. 18-19 disclose cannulae with dovetail notches for holding embedded steering elements.
Figure 19:
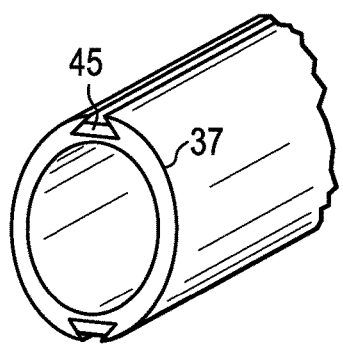

The tool of the present invention may further include bilateral pulling strips running alongside the cannula to steer the tool. In the intradiscal environment, the active steering force needs to be high (depending on the cutting ability and the resistance within the tissue). Now referring to FIGS. 12-17, in one preferred embodiment, pulling strips 43 are arranged along both the left and the right side of the cannula, and are guided through notches 45. When pulled on the left string, the flexible steering cannula (SC) will bend to the left side, and vice versa (see FIG. 12). In some embodiments, the pulling strip 43 can be disposed on the inside of the steering cannula (see FIG. 13). In some embodiments, the pulling strips 43 are integrated into the cannula wall 47 via notches. The cannula wall thickness has to be as small as possible, in order to have as much cross sectional area as possible in the inner lumen (FIGS. 16-17). The "notch" embodiments allow the cannula inner lumen to be as large as possible to allow the rotating member to contain irrigation, torque transmission and the transport auger)

In other embodiments, the steering is accomplished by using a pushing force. This preferably occurs without uncontrolled deformation of the strip. The ability of the steering to accomplish these goals is due to the dovetail feature.

Referring now to FIGS. 12-19, there is provided a discectomy tool comprising a) a cannula 31 having a proximal end portion 33, a distal end portion 35, and an outer surface 37;

b) a transmission shaft disposed in the cannula, the shaft having a proximal end portion and a distal end portion;

c) a cutting tip attached to the distal end portion of the transmission shaft;

d) first and second steering elements 43 bilaterally and longitudinally disposed on the outer surface of the cannula.

Figure 14:
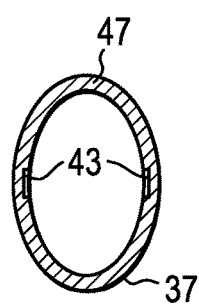
FIGS. 14-15 disclose cross-section of cannulae of the present invention with embedded steering elements.

In some embodiments, longitudinal notches 45 are provided on the inner steering cannula wall 49 (see FIG. 14). This embodiment, however, may be a production challenge, since EDM or profile extrusion are expensive. To have the notch on the outside surface 37 of the cannula (see FIG. 15) would offer an easier manufacturing. Moreover, its lever ratio would be more beneficial (more side bending force at the same pulling strength).

Figure 15:
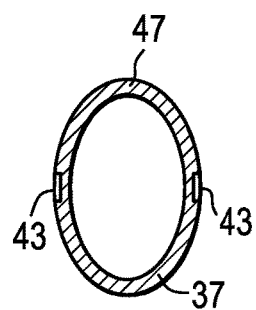

Referring now to FIG. 15, there is provided a discectomy tool comprising:

a) a cannula having a proximal end, a distal end, and an outer surface having a first longitudinal recess (notch) therein;
b) a transmission shaft disposed in the cannula, the shaft having a proximal end portion and a distal end portion;
c) a cutting tip attached to the distal end portion of the transmission shaft;
d) a first steering element disposed in the first longitudinal recess of the outer surface.

Without wishing to be tied to a theory, it is believed that simply making the notch 45 a rectangular shape would easily allow the pulling strings to fall out. Therefore, one solution regarding steering force and manufacturing possibilities is a dovetail-like profile notch that is easily retains the like-shaped steering strip. More generally, the dovetail is one example in which the first longitudinal recess has a tranverse opening at the outer surface and the steering element has a maximum transverse cross-section, wherein the maximum cross-section is greater than the opening of the recess at the outer surface, thereby preventing expulsion of the steering element from the recess.

Figure 20:
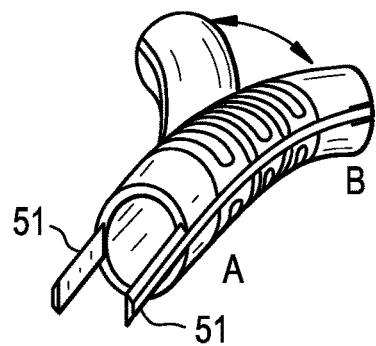
FIGS. 20-22 disclose cannulae in which the steering elements are metallic/polymeric tapered strips.
Figure 21:
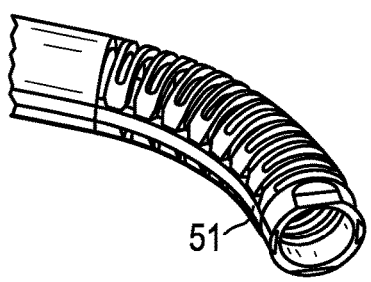
Figure 22:
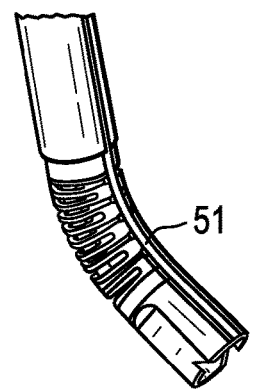

Now referring to FIGS. 20-22, in some embodiments, the steering elements are flat metallic/polymeric tapered strips 51. They have the mechanical property of being very flexible in up-down bending, but quite stable in lateral bending. This lateral bending stability of the steering strips is essential to increase the torsional stability of the outer cannula assembly. A further advantage of flat steering strips is that the wall thickness of the outer cannula can be very small. Such steering strips have the big advantage that simultaneous pulling on one string and pushing on the other string increases the steering force and keeps the length of the neutral axis of the steering cannula constant in length if it is steered. In contrast, in many other conventional tools, steering is limited to only pulling and uses only a single pulling strip. Thus, in the present invention, there is much more defined motion, which is important in navigation.

Figure 23:
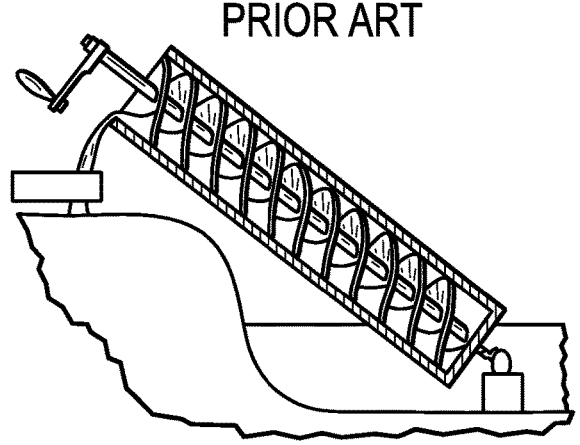
FIG. 23 is a prior art Archimedes pump.

A common challenge in discectomies is to not only to cut and detach disc material from the disc proper, but also to transport the excised disc material automatically out of the body. It is important to prevent the tissue from clogging the tool. Auger systems (modeled after the Archimedes pump shown in FIG. 23) have been proposed to achieve these goals. However, wishing to be tied to a theory, it is believed that a simple Archimedes pump itself might not be sufficient to guarantee a proper transport of the cut disc material fragment, as the disc material might get dry and stick to the auger walls, which finally leads to a clogging of several fragments and a transport interruption.

Figure 24:
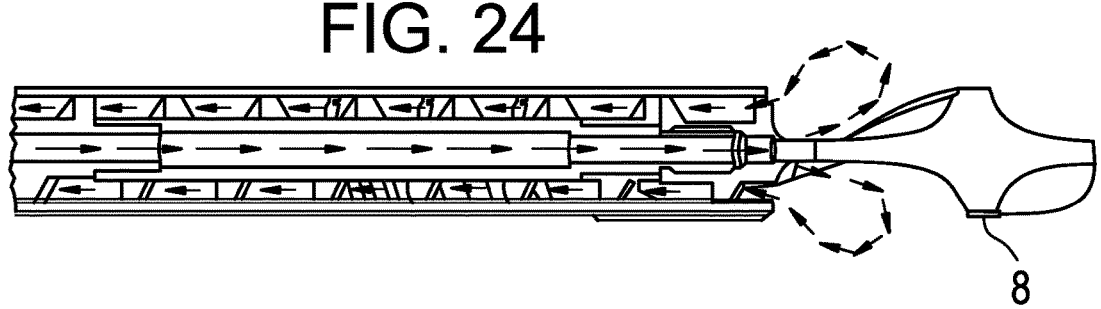
FIG. 24 is a tool of the present invention having integrated irrigation flow.

In order to prevent this clogging, and now referring to FIG. 24, some embodiments of the present invention integrates irrigation flow from an irrigation flow means (not shown) into the tool. The inflow can be performed either between the outer cannula of the disc removal device and the working channel, or through a central lumen inside the auger. With irrigation through an inner lumen, the exit point of the inflow can be located close to the cutting blade or from within the cutting blade. This allows having a permanent inflow over the blade geometries during the cutting, and helps to keep the blade clean. If the blade can not be kept clean, especially sharp edges can get covered with disc tissue and decrease the cutting ability of the blade.

It is believed that a smooth continuous transport geometry without sudden transitions is desirable to reach a reliable transport of the cut disc material fragments. However, in use, in the steerable area of the transmission shaft, the bending radius can be below 15 mm. Thus, it is desired to provide a tool that provides small bending radii, smooth auger geometry transition and adequate torque transmission. One solution is to provide a flexible torque transmission shaft overlayed by, but not directly connected to, a flexible auger element. It is believed that if directly connected at the flexible/steerable area, the construct would lose a certain amount of its flexibility, so transitional movements between the flexible torque transmission shaft and the flexible auger do have to be possible. The "loose" auger avoids this problem.

However, the flexible auger is preferably connected with the cutting blade on its distal end, and with the straight/stiff threaded shaft on its proximal end, and allows very smooth geometrical transitions between these different elements in order to prevent obstacles for a reduced resistance tissue/material transport from the cutting blade along to the auger flanks.

The flexible auger portion can comprise either:
a) polymeric or metal spiral alone, in case of very low torque transmission: (see FIG. 25);
b) a polymeric spiral connected to a tube which is connected to the inner shaft at an extension, but not along the flexible/steering zone (decreases bending stiffness), in case of higher torque transmission (see FIG. 26))

Figure 25:
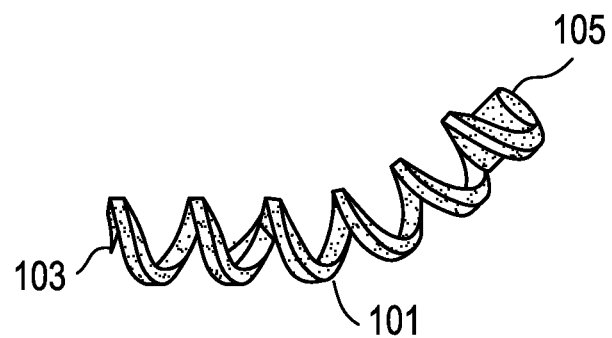
FIG. 25 discloses an embodiment of a helical spiral transmission shaft of the present invention.

Now referring to FIG. 25, there is provided a discectomy tool comprising:
a) a cannula having an outer surface having a longitudinal bore therein, a proximal end and a distal end;
b) a transmission shaft having a proximal end portion and a distal end portion;
c) a rotatable cutting tip having a proximal end portion; and
d) a flexible helical auger 101 having a proximal end portion 103 and a distal end portion 105, wherein the proximal end portion of the auger is connected to the transmission shaft, and wherein the distal end portion of the auger is connected to the proximal end portion of the cutting tip
wherein the transmission shaft and auger are adapted to rotate within the longitudinal bore of the cannula,
wherein the cutting tip extends out the bore at the distal end of the cannula.

In some embodiments, the auger can be manufactured by attaching a flexible (e.g., PEEK) auger to a metal (preferably threaded) transmission shaft.

Figure 26:
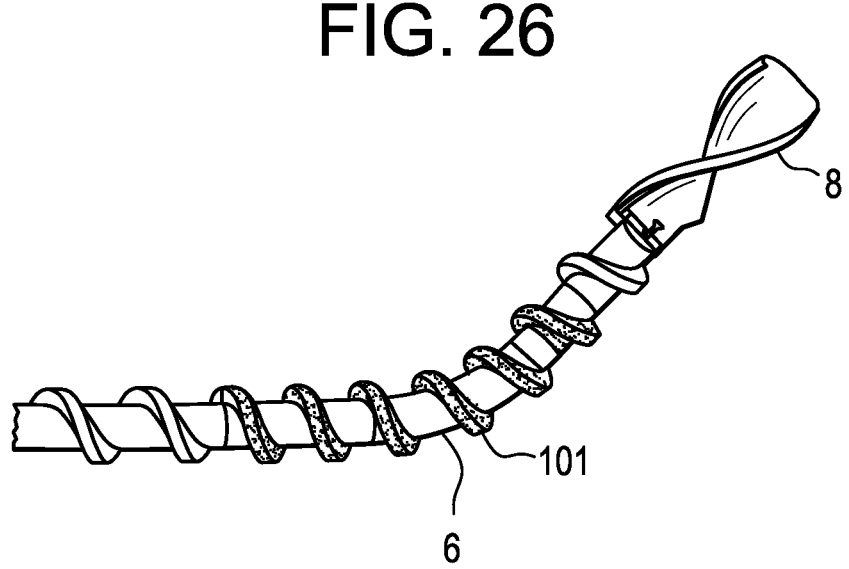
FIG. 26 discloses an embodiment of a helical spiral loosely connected to a transmission shaft of the present invention.

Referring now to FIG. 26, there is provided a discectomy tool comprising:
a) a cannula having an outer surface having a longitudinal bore therein, a proximal end and a distal end;
b) a transmission shaft having a proximal end portion and a distal end portion;
c) a rotatable cutting tip attached to the distal end portion of the transmission shaft; and
d) a flexible helical auger having a proximal end portion, and intermediate portion and a distal end portion, wherein the intermediate portion is loosely wrapped around the flexible torque transmission shaft, wherein the proximal end portion of the auger is connected to the transmission shaft, and wherein the distal end portion of the auger is connected to the proximal end portion of the cutting tip,
wherein the transmission shaft and auger are adapted to rotate within the longitudinal bore of the cannula, wherein the cutting tip extends out the bore at the distal end of the cannula.

The loose auger in this flexible torque transmission shaft can be provided in a number of ways, such as the following non-limiting examples:
a) narrow spring,
b) solid tube shaft of flexible material,
c) solid metal shaft with specific cutouts to become flexible in bending etc.)

For the outflow, a suction device can be connected with the auger/transport lumen so that a continuous liquid flow is helping to transport the cut disc material fragments.

In some embodiment, the tool has a safety housing to prevent cutting of anatomic elements outside of the intervertebral disc, as, for example, the endplates of the adjacent vertebrae. With a safety housing, the blade is only able to cut to one side, and not to progress in depth. After an initial cylindrical hole is drilled (with a standard drill), the tip of the disc removal device can be inserted until it touches the ground of the hole. After this, the tip can only be steered to one direction. This means that if the depth of the initial drilled hole determines the reachable area of the cutting tip.

We claim:

1. A discectomy tool comprising:
a cannula having an outer surface having a longitudinal bore therein, a proximal end and a distal end;
a transmission shaft having a proximal end portion and a flexible distal end portion, wherein the transmission shaft includes a central throughbore which extends therealong;
a rotatable cutting tip attached to the flexible distal end portion of the transmission shaft; and
a flexible helical auger having a proximal end portion, an intermediate portion, and a distal end portion, wherein the proximal end portion of the auger is directly connected to the proximal end portion of the transmission shaft such that relative rotation between the proximal end portion of the auger and the proximal end portion of the transmission shaft is prevented, the intermediate portion is loosely wrapped around the flexible distal end portion of the transmission shaft between the proximal end portion and the distal end portion to allow transitional movement between the torque transmission shaft and the flexible helical auger, and the distal end portion of the auger is directly connected to the cutting tip such that relative rotation between the distal end portion of the auger and the cutting tip is prevented,
wherein the flexible helical auger is a solid tube shaft of flexible material that is coaxial with the transmission shaft, and
wherein the transmission shaft and the auger are adapted to rotate within the longitudinal bore of the cannula, wherein the cutting tip extends out the bore at the distal end of the cannula.

2. The tool of claim 1, wherein the distal end portion of the auger is connected to a proximal end portion of the cutting tip.

3. The tool of claim 1, wherein the auger is made of PEEK and the transmission shaft is made of a metal.

4. A discectomy tool comprising:
a cannula having an outer surface having a longitudinal bore therein, a proximal end and a distal end;
a transmission shaft having a proximal end portion and a flexible distal end portion, wherein the transmission shaft includes a central throughbore which extends therealong;
a rotatable cutting tip attached to the flexible distal end portion of the transmission shaft; and
a flexible helical auger having a proximal end portion, a hollow intermediate portion configured to allow transitional movement with respect to the transmission shaft, and a distal end portion, wherein the proximal end portion of the auger is directly connected to the proximal end portion of the transmission shaft such relative rotation between that the proximal end portion of the auger and the proximal end portion of the transmission shaft is prevented and the distal end portion of the auger is directly connected to the cutting tip such that relative rotation between the distal end portion of the auger and the cutting tip is prevented,
wherein the flexible helical auger is a solid tube shaft of flexible material that is coaxial with the transmission shaft, and
wherein the transmission shaft and the auger are adapted to rotate within the longitudinal bore of the cannula, wherein the cutting tip extends out the bore at the distal end of the cannula.

5. The tool of claim 4, wherein the auger is made of PEEK and the transmission shaft is made of a metal.

* * * * *